United States Patent [19]

Miki et al.

[11] Patent Number: 5,268,512

[45] Date of Patent: Dec. 7, 1993

[54] CATALYST AND PROCESS FOR PRODUCING PHENOL

[75] Inventors: Jun Miki; Toshifumi Suzuki; Tsutomu Shikada; Kazuhiko Tate; Yakudo Tachibana, all of Tokyo, Japan

[73] Assignee: NKK Corporation, Tokyo, Japan

[21] Appl. No.: 954,794

[22] Filed: Jul. 10, 1992

Related U.S. Application Data

[62] Division of Ser. No. 679,850, Apr. 3, 1991, abandoned.

[30] Foreign Application Priority Data

| Apr. 17, 1990 | [JP] | Japan | 2-99333 |
| Jul. 30, 1990 | [JP] | Japan | 2-199161 |
| Dec. 11, 1990 | [JP] | Japan | 2-401303 |
| Dec. 27, 1990 | [JP] | Japan | 2-408265 |
| Dec. 27, 1990 | [JP] | Japan | 2-408266 |
| Dec. 27, 1990 | [JP] | Japan | 2-408267 |
| Dec. 27, 1990 | [JP] | Japan | 2-408268 |

[51] Int. Cl.$^5$ .................... C07C 37/055; C07C 37/00
[52] U.S. Cl. .................... 568/801; 568/800; 502/201; 502/208; 502/330
[58] Field of Search ............... 568/801, 800; 502/330, 502/201, 208

[56] References Cited

U.S. PATENT DOCUMENTS

| 1,961,912 | 6/1934 | Querfurth | 502/337 |
| 3,308,167 | 3/1967 | Costabello et al. | 568/801 |
| 3,957,804 | 5/1976 | Ishioka et al. | 502/337 |
| 3,959,181 | 5/1976 | Boerma | 252/459 |
| 4,009,126 | 2/1977 | McFarland | 502/328 |
| 4,042,490 | 8/1977 | Suggitt et al. | 502/330 |
| 4,085,193 | 4/1978 | Nakajima et al. | 502/330 |
| 4,215,018 | 7/1980 | Dorowala et al. | 502/330 |
| 4,225,732 | 9/1980 | Oabrowski | 568/794 |
| 4,567,157 | 1/1986 | Lam et al. | 568/801 |
| 4,620,043 | 10/1986 | Lam et al. | 568/801 |
| 4,988,661 | 1/1991 | Arai et al. | 502/328 |

FOREIGN PATENT DOCUMENTS

| 0002575 | 6/1979 | European Pat. Off. |
| 2280428 | 2/1976 | France |
| 2358924 | 2/1978 | France |

*Primary Examiner*—Werren B. Lone
*Attorney, Agent, or Firm*—Sughrue, Mion, Zinn, Macpeak & Seas

[57] ABSTRACT

A catalyst for producing phenol consisting essentially of a nickel compound supported on a metal oxide carrier, or a catalyst for producing phenol consisting essentially of iron oxide and nickel oxide, and processes for producing phenol using either of the above catalyst. The catalysts of the invention exercise a high conversion of benzoic acid and a high selectivity to phenol, and phenol can be produced in a high yield, particularly in a high space time yield through the processes of the invention using the above catalysts. The above conversion, selectivity and space time yield can be improved by calcining the catalyst at 600° to 900° C.

40 Claims, No Drawings

CATALYST AND PROCESS FOR PRODUCING PHENOL

This is a divisional of application Ser. No. 07/679,850 filed Apr. 3, 1991, abandoned.

BACKGROUND OF THE INVENTION

This invention relates to catalysts for producing phenol and processes for producing phenol from benzoic acid through vapor phase oxidation in the presence of the catalyst.

Heretofore, various catalysts and processes were developed for producing phenol from benzoic acid through catalytic oxidation in vapor phase. For example, Japanese Patent KOKAI No. 57-11932 discloses a catalyst for producing phenol composed of at least one of copper compounds, vanadium compounds, silver compounds, lithium compounds, sodium compounds and magnesium compounds, and a process for producing phenol using the above catalyst. Another catalyst and process are disclosed in Japanese Patent KOKOKU No. 59-20384. The catalyst contains oxidized copper, zirconium and alkali metal, and the process uses them supported on α-alumina carrier as the catalyst. Moreover, Japanese Patent KOKOKU No. 64-934 discloses a process for producing phenol using an oxide catalyst composed of many kinds of metal elements, i.e. molybdenum as the essential element, at least one of vanadium, niobium and tantalum, at least one of copper, silver, manganese, iron, cobalt, nickel, rhodium, palladium and platinum, and at least one of thallium, alkali metals and alkaline earth metals.

However, the catalyst disclosed in Japanese Patent KOKAI No. 57-11932 is insufficient in the yield of phenol. Actually, the maximum conversion of benzoic acid was 50.5%, and the maximum selectivity to phenol was 88.6%, and therefore, the maximum yield was 44.7%. Besides, when an exothermic reaction is conducted such as the oxidation reaction of benzoic aicd using the catalyst containing a copper compound, hot spots occur in the catalyst layer to progress calcining of the catalyst. As a result, the catalytic activity is degraded sharply. In the manufacturing process disclosed in Japanese Patent KOKOKU No. 59-20384, the yield of phenol is insufficient. That is, the maximum conversion of benzoic acid was 63.7%, and the maximum selectivity to phenol was 82.2%, and therefore, the maximum yield was 52.4%. Moreover, byproducts such as diphenyl oxide are produced abundantly, and therefore, a purification process for the produced phenol is necessary. In the manufacturing process disclosed in Japanese Patent KOKOKU No. 64-934, the maximum conversion of benzoic acid was 75%, and the maximum selectivity to phenol was 89%. Therefore, the maximum yield was 66.8%. Moreover, all of the above conventional processes are inferior in productivity due to low space time yield (the production amount of phenol per unit volume of catalyst per unit time), and therefore, they are disadvantageous in the industrial production of phenol.

SUMMARY OF THE INVENTION

An object of the invention is to provide a catalyst capable of producing phenol from benzoic acid in a high yield.

Another object of the invention is to provide a catalyst having a high conversion and capable of producing phenol from benzoic acid in a high yield.

Another object of the invention is to provide a catalyst having a high selectivity and capable of producing phenol from benzoic acid in a high yield.

Another object of the invention is to provide a catalyst having a high conversion and a high selectivity and capable of producing phenol from benzoic acid in a high yield.

Another object of the invention is to provide a catalyst resistant to a high temperature capable of producing phenol from benzoic acid in a high yield in a high space time yield.

Another object of the invention is to provide a process capable of producing phenol from benzoic acid through vapor phase oxidation in a high yield.

Another object of the invention is to provide a process capable of producing phenol from benzoic acid through vapor phase oxidation in a high yield with less production of byproducts.

Another object of the invention is to provide a process capable of producing phenol from benzoic acid through vapor phase oxidation in a high yield in a high space time yield.

The present invention provides the following catalysts and the processes which have achieved the above objects.

A catalyst for producing phenol consists essentially of a nickel compound supported on a metal oxide carrier.

A catalyst for producing phenol consists essentially of iron oxide and nickel oxide.

A catalyst for producing phenol consists essentially of iron oxide, nickel oxide and an alkali metal compound.

A catalyst for producing phenol consists essentially of iron oxide, nickel oxide and an alkaline earth metal compound.

A catalyst for producing phenol consists essentially of iron oxide, nickel oxide, an alkali metal compound and an alkaline earth metal compound.

A process for producing phenol from benzoic acid through vapor phase oxidation using at least one of the above catalysts.

DETAILED DESCRIPTION OF THE INVENTION

The nickel compound supported on a metal oxide carrier include oxide, hydroxide, carbonate, nitrate, chloride, carbide, nitride, and sulfide, and oxide is preferred because stable activity can be exercised from the initial stage.

The metal oxide carrier is titania, magnesia, α-alumina, silica gel, zirconia, tin oxide, lantharum oxide and the like, and titania, magnesia and α-alumina are preferred in view of high conversion and high selectivity.

The conversion of benzoic acid can be improved by adding an alkali metal compound or an alkaline earth metal compound. The alkali metal compound is oxide, carbonate, hydroxide, nitrate or the like, and preferable compounds are oxides such as $Li_2O$, $Na_2O$, $K_2O$, $Rb_2O$ and $Cs_2O$, and $Na_2O$ and $K_2O$ are particularly preferred in view of the low production of CO and $CO_2$ and the high selectivity to phenol. The alkaline earth metal compound is also oxide, carbonate, hydroxide, nitrate or the like, and preferable compounds are oxides such as MgO, CaO, SrO and BaO, and CaO is particularly preferred.

A suitable content of the nickel compound is about 0.5 to 50 wt. %, preferably 2 to 20 wt. %. When the content is less than 0.5 wt. %, the conversion of benzoic acid is low. While, when the content is beyond 50 wt. %, the production of CO and $CO_2$ increases by the complete combustion resulting to reduce the selectivity to phenol. A suitable content in the sum of the alkali metal compound and the alkaline earth metal compound is about 0.1 to 30 wt. %, preferably 0.5 to 5 wt. %.

The nickel compound can be supported on the metal oxide carrier by utilizing a conventional impregnation technique. The alkali metal compound and the alkaline earth metal compound may be added to the catalyst before, after or during supporting the nickel compound on the metal oxide carrier.

The catalyst composition prepared by the impregnation is dried in the atmosphere at 90° to 150° C. for 12 to 36 hours. The dried matter may be calcined in the atmosphere or a nitrogen gas atmosphere at 400° to 1,000° C. for 1 to 10 hours.

In the catalyst composed of iron oxide and nickel oxide, a suitable ratio of nickel oxide/iron oxide is 0.1 to 10, preferably 0.3 to 5, more preferably 0.5 to 2 by weight. When the ratio of nickel oxide/iron oxide is greater than 10, the production of CO and $CO_2$ increases by the complete combustion resulting to reduce the selectivity to phenol. While, when the ratio is less than 0.1, the production of benzene increases resulting to reduce the selectivity to phenol. Most of the iron oxide may be $Fe_2O_3$, and most of the nickel oxide may be NiO, according to the preparation process of the catalyst.

The conversion of benzoic acid and the selectivity to phenol can be improved by adding an alkali metal compound, an alkaline earth metal compound or both of them.

Suitable alkali metal compounds and alkaline earth metal compounds and preferred ones are the same as aforementioned.

A suitable content of the alkali metal compound and that of the alkaline earth metal compound are about 0.05 to 30 wt. %, preferably 0.1 to 10 wt. %, as the value converted to the oxide thereof, respectively. When the content is less than 0.05 wt. %, the production of CO and $CO_2$ increases resulting to reduce the selectivity to phenol. While, when the content is beyond 30 wt. %, the conversion of benzoic acid decreases. In the case of adding both of the alkali metal compound and the alkaline earth metal compound, each suitable content of both compounds converted to the oxide thereof is about 0.01 to 20 wt. %, preferably 0.05 to 5 wt. %, respectively.

The nickel oxide-iron oxide catalyst may contain other various compounds, and may be supported on a carrier such as titania or silica.

The above nickel oxide-iron oxide catalysts can be prepared according to a known method for preparing conventional catalysts. That is, the raw materials of iron oxide and nickel oxide may be nitrate, carbonate, organic acid salt, halide, hydroxide, oxide or the like. The iron compound and the nickel compound is mixed by a conventional method such as precipitation, kneading, impregnation or the like. Alternatively, iron oxide powder is mixed with nickel oxide powder, and the powder mixture may be pelletized by pressing. When the alkali metal compound or the alkaline earth metal compound is incorporated into the catalyst, for example, the alkali metal compound or the alkaline earth metal compound may be added to a gel mixture of iron hydroxide and nickel hydroxide as it is or in a state of a solution. Then, the mixture is dried and calcined. Besides, the alkali metal compound or the alkaline earth metal compound may be added to the mixture of iron oxide and nickel oxide, or may be added to the calcined mixture of iron oxide and nickel oxide by blending or impregnation. Furthermore, a mixture of iron oxide powder, nickel oxide powder and the alkali metal compound powder or the alkaline earth metal compound powder is prepared, and the powder mixture may be pelletized by pressing.

During preparing the iron oxide-nickel oxide catalysts of the invention, it is preferable to calcine iron oxide or a precursor thereof and nickel oxide or a precursor thereof, after they are mixed with each other. The calcination is conducted at about 600° to 900° C., preferably 650° to 850° C. in the atmosphere or an inert gas atmosphere so as to crystallize at least one of iron oxide, nickel oxide and iron-nickel complex oxide. In general, when a catalyst prepared by a conventional method is calcined at a temperature higher than about 600° C. the catalytic activity decreases due to the decrease of specific surface area. However, in the case of the iron oxide-nickel oxide catalysts of the invention, phenol-producing activity is improved to obtain a high conversion of benzoic acid and a high selectivity to phenol by the calcination at about 600° to 900° C., although the specific surface area is decreased. When the calcination temperature is lower than about 600° C., only CO and $CO_2$ production proceeds by the complete combustion. Phenol is produced little, and carbonaceous materials deposit on the surface of the catalyst. While, when the calcination temperature is higher than about 900° C., the conversion of benzoic acid is sharply reduced, and the production of phenol is minor.

Phenol is produced from benzoic acid in the presence of at least one of the aforementioned catalyst, and at that time, oxygen gas is supplied together with benzoic acid. The supply amount of oxygen gas is more than the theoretical amount against the supply amount of benzoic acid, and about 0.5 to 50 times moles is preferred. When the supply amount of oxygen gas is more than 50 times that of benzoic acid, the complete combustion of benzoic acid frequently occurs. While, when the supply amount of oxygen gas is less than 0.5 times, sufficient conversion of benzoic acid cannot occur. The oxygen gas may be in a form of air or pure oxygen gas, and they may be diluted with an inert gas.

The reaction is, in general, conducted in the presence of water vapor, and the supply amount of water vapor is preferably about 1 to 100 times that of benzoic acid in a molar ratio. The supply amount beyond about 100 times is disadvantageous in an economical viewpoint. While, when the supply amount is less than about one time, the selectivity to phenol is degraded. The space velocity of the reaction gas, i.e. the sum of benzoic acid, oxygen-containing gas and water vapor, is preferably about 100 to 50,000 $hr^{-1}$, more preferably 2,000 to 20,000 $hr^{-1}$, furthermore preferably 5,000 to 20,000 $hr^{-1}$. When the space velocity is less than about 100 $hr^{-1}$, the space time yield is insufficient. While, when the space velocity is beyond about 50,000 $hr^{-1}$, the conversion of benzoic acid is low. The reaction temperature is usually about 200° to 600° C., and about 350° to 500° C. is preferred. When the reaction temperature is higher than about 600° C., the selectivity to phenol decreases. While, when the reaction temperature is lower than about 200° C., the conversion of benzoic acid is insufficient. The reaction pressure may be any pressure capable of keeping the supplied raw materials in a vapor state, and it is usually ordinary pressure or slightly pressurized condition.

The reaction apparatus may be fixed bed type or fluidized bed type.

The catalysts of the invention exercise a high conversion of benzoic acid and a high selectivity to phenol, and phenol can be produced in a high yield, particularly in a high space time yield through the processes of the invention using the above catalysts.

EXAMPLES

Examples 1,2

38.9 g of nickel nitrate ($Ni(NO_3)_2.6H_2O$) was dissolved in 300 cc of pure water purified by using ion exchange resins, and 188 g of titanium dioxide was added to the solution with stirring. The suspension was evaporated and dried at 120° C. The dried matter was calcined in the atmosphere at 500° C. for 3 hours, and crushed into a prescribed mesh. The catalyst powder was impregnated in a potassium hydroxide solution containing 2.4 g of potassium hydroxide dissolved in pure water, and dried at 120° C. The catalyst powder was calcined again in the atmosphere at 500° C. for 3 hours to obtain a catalyst composed of nickel oxide, potassium oxide and titanium dioxide in the ratio by weight of 5:1:94 as the ratio of $NiO:K_2O:TiO_2$.

Example 3-5

77.8 g of nickel nitrate ($Ni(NO_3)_2.6H_2O$) was dissolved in 300 cc of pure water, and 180 g of titanium dioxide was impregnated in the solution with stirring. After drying at 120° C., the dried matter was calcined in the atmosphere at 500° C. for 3 hours to obtain a catalyst having a ratio by weight of 10:90 as $NiO:TiO_2$.

Examples 6,7

3.9 g of nickel nitrate and 5.1 g of iron nitrate ($Fe(NO_3)_3.9H_2O$) were dissolved in 30 cc of pure water, and 18 g of titanium dioxide was impregnated in the solution with stirring. After drying at 120° C., the dried matter was calcined in the atmosphere at 500° C. for 3 hours to obtain a catalyst having a ratio by weight of 5:5:90 as $NiO:Fe_2O_3:TiO_2$.

Comparative Example 1

200 g of nickel nitrate was dissolved in 500 ml of pure water, and about 100 g of sodium hydroxide was dissolved in 500 ml of pure water. Both solutions were added dropwise to 2 l of pure water so as to maintain pH 7-8. After adding, the mixture was stirred for about 1 hour. The precipitates produced were filtered and washed. The cake was dried in the atmosphere at 120° C. for 24 hours, and then calcined in the atmosphere at 800° C. for 4 hours to obtain a catalyst.

Comparative Example 2

A catalyst was prepared according to Example 1 described in Japanese Patent KOKOKU No. 64-934.

Comparative Example 3

A catalyst was prepared according to Reference Example 1 described in Japanese Patent KOKOKU No. 59-20384.

Comparative Example 4

200 g of iron nitrate was dissolved in 500 ml of pure water, and about 100 g of sodium hydroxide was dissolved in 500 ml of pure water. Both solutions were added dropwise to 2 l of pure water so as to maintain pH 7-8. After adding, the mixture was stirred for about 1 hour. The precipitates produced were filtered and washed. The cake was dried in the atmosphere at 120° C. for 24 hours, and then calcined in the atmosphere at 800° C. for 4 hours to obtain a catalyst.

Production of Phenol

Each catalyst was crushed and sieved to a prescribed mesh, and the amount described in Table 1 or 2 was placed in a quartz tube having an inner diameter of 20 mm. Benzoic acid, water vapor, air and nitrogen gas were supplied at the rate described in Table 1 or 2, and allowed to react at the temperature described in Table 1 or 2.

The experimental results are summarized in Table 1 and 2.

TABLE 1

|  | Example 1 | Example 2 | Example 3 | Example 4 | Example 5 | Example 6 | Example 7 |
|---|---|---|---|---|---|---|---|
| Catalyst Composition (wt. %) | $NiO-K_2O-TiO_2$ (5:1:94) | $NiO-K_2O-TiO_2$ (5:1:94) | $NiO-TiO_2$ (10:90) | $NiO-TiO_2$ (10:90) | $NiO-TiO_2$ (10:90) | $NiO-Fe_2O_3-TiO_2$ (5:5:90) | $NiO-Fe_2O_3-TiO_2$ (5:5:90) |
| Catalyst Amount (g) | 20 | 20 | 20 | 5 | 5 | 20 | 5 |
| Reaction Temperature (°C.) | 400 | 400 | 400 | 400 | 450 | 400 | 400 |
| Supply Rate of Benzoic Acid ($10^{-4}$ mol/min) | 1.45 | 1.45 | 1.45 | 0.55 | 0.55 | 1.45 | 2.70 |
| Supply Rate of Water Vapor ($10^{-3}$ mol/min) | 4.35 | 4.35 | 1.45 | 1.10 | 1.10 | 1.45 | 8.10 |
| Supply Rate of Air (cc/min) | 20 | 16 | 32 | 6 | 6 | 32 | 12 |
| Supply Rate of Nitrogen Gas (cc/min) | 16 | 16 | 49 | 18 | 18 | 49 | 60 |

TABLE 1-continued

|  | Example 1 | Example 2 | Example 3 | Example 4 | Example 5 | Example 6 | Example 7 |
|---|---|---|---|---|---|---|---|
| Conversion of Benzoic Acid (%) | 95 | 87 | 54 | 10 | 58 | 49 | 25 |
| Selectivity (%) | | | | | | | |
| Phenol | 64 | 69 | 73 | 75 | 57 | 75 | 75 |
| Benzene | 25 | 20 | 20 | 18 | 37 | 23 | 11 |
| CO, $CO_2$ | 3 | 1 | 6 | tr | 1 | 1 | 11 |
| Yield of Phenol (%) | 95 × 0.64 | 87 × 0.69 | 54 × 0.73 | 10 × 0.75 | 58 × 0.57 | 49 × 0.75 | 25 × 0.75 |

TABLE 2

|  | Comparative 1 | Comparative 2 | Comparative 3 | Comparative 4 |
|---|---|---|---|---|
| Catalyst Composition (wt. ratio) | NiO (100) | $MoO_3$—$V_2O_5$—CuO—$Na_2O$—$Al_2O_3$ (3.9:3.7:3.8:4.9:82.7) | CuO—ZrO—$K_2O$—$Al_2O_3$ (4.0:3.0:3.6:89.4) | $Fe_2O_3$ (100) |
| Catalyst Amount (g) | 5 | 5 | 5 | 5 |
| Catalyst Calcining Temperature (°C.) | 800 | 600 | 500 | 800 |
| Reaction Temperature (C.) | 400 | 300 | 300 | 400 |
| Supply Rate of Benzoic Acid ($10^{-4}$ mol/min) | 2.70 | 2.70 | 2.70 | 2.70 |
| Supply Rate of Water Vapor ($10^{-3}$ mol/min) | 8.10 | 8.10 | 8.10 | 8.10 |
| Supply Rate of Air (cc/min) | 12 | 12 | 12 | 12 |
| Supply Rate of Nitrogen Gas (cc/min) | 60 | 60 | 60 | 60 |
| Conversion of Benzoic Acid (%) | 8 | 48 | 25 | 0.1 |
| Selectivity (%) | | | | |
| Phenol | 15 | 80 | 70 | 10 |
| Benzene | 16 | 3 | 5 | 3 |
| CO, $CO_2$ | 68 | 16 | 19 | 85 |
| Yield of Phenol (%) | 8 × 0.15 | 48 × 0.80 | 25 × 0.70 | 0.1 × 0.10 |

Example 8,9

200 g of iron nitrate ($FE(NO_3)_3 \cdot 9H_2O$) and 154 g of nickel nitrate ($Ni(NO_3)_2 \cdot 6H_2O$) were dissolved in 500 ml of pure water, and about 100 g of sodium hydroxide was dissolved in 500 ml of pure water. Both solutions were added dropwise to 2 l of pure water at ordinary temperature so as to maintain pH 7-8. After adding, the mixture was stirred for about 1 hour. The precipitates produced were filtered and washed. The cake was dried in the atmosphere at 120° C. for 24 hours, and then calcined in the atmosphere at 800° C. for 4 hours to obtain a catalyst having a ratio by weight of 50:50 as $NiO:Fe_2O_3$.

Example 10

Using 59 g of nickel nitrate and 328 g of iron nitrate, a catalyst was prepared in the same method as Examples 8,9. The catalyst obtained had a ratio by weight of 19:81 as $NiO:Fe_2O_3$.

Example 11

Using 108 g of nickel nitrate and 200 g of iron nitrate, a catalyst was prepared in the same method as Examples 8,9. The catalyst obtained had a ratio by weight of 44:56 as $NiO:Fe_2O_3$.

Example 12

Using 202 g of nickel nitate and 142 g of iron nitrate, a catalyst was prepared in the same method as Examples 8,9. The catalyst obtained had a ratio by weight of 65:35 as $NiO:Fe_2O_3$.

Example 13

Except that the calcining temperature was set at 700° C., a catalyst was prepared in the same method as Examples 8,9.

Example 14

Except that the calcining temperature was set at 600° C., a catalyst was prepared in the same method as Examples 8,9.

Example 15

Except that the calcining temperature was set at 500° C., a catalyst was prepared in the same method as Examples 8,9.

Example 16

Except that the calcining temperature was set at 400° C., a catalyst was prepared in the same method as Examples 8,9.

Example 17

Except that the calcining temperature was set at 1,000° C., a catalyst was prepared in the same method as Examples 8,9.

Production of Phenol

Each catalyst was crushed and sieved to a prescribed mesh, and the amount described in Table 3 was placed in a quartz tube having an inner diameter of 20 mm. Benzoic acid, water vapor, air and nitrogen gas were supplied at the rate described in Table 3, and allowed to react at the temperature described in Table 3.

The experimental results are summarized in Table 3.

TABLE 3-1

|  | Example 8 | Example 9 | Example 10 | Example 11 | Example 12 |
| --- | --- | --- | --- | --- | --- |
| Catalyst Composition (wt. ratio) | NiO—$Fe_2O_3$ (50:50) | NiO—$Fe_2O_3$ (50:50) | NiO—$Fe_2O_3$ (19:81) | NiO—$Fe_2O_3$ (44:56) | NiO—$Fe_2O_3$ (65:35) |
| Catalyst Amount (g) | 20 | 5 | 20 | 20 | 20 |
| Catalyst Calcining Temperature (°C.) | 800 | 800 | 800 | 800 | 800 |
| Reaction Temperature (C.) | 400 | 400 | 400 | 400 | 400 |
| Supply Rate of Benzoic Acid ($10^{-4}$ mol/min) | 1.20 | 1.20 | 1.60 | 1.20 | 1.40 |
| Supply Rate of Water Vapor ($10^{-3}$ mol/min) | 3.60 | 6.00 | 6.00 | 3.60 | 6.35 |
| Supply Rate of Air (cc/min) | 27 | 27 | 27 | 27 | 27 |
| Supply Rate of Nitrogen Gas (cc/min) | 40 | 40 | 40 | 40 | 40 |
| Conversion of Benzoic Acid (%) | 100 | 94 | 62 | 87 | 46 |
| Selectivity (%) |  |  |  |  |  |
| Phenol | 93 | 86 | 25 | 78 | 73 |
| Benzene | 5 | 11 | 75 | 18 | 15 |
| CO, $CO_2$ | 1 | 2 | tr | 3 | 8 |
| Yield of Phenol (%) | 100 × 0.93 | 94 × 0.86 | 62 × 0.25 | 87 × 0.78 | 46 × 0.73 |

TABLE 3-2

|  | Example 13 | Example 14 | Example 15 | Example 16 | Example 17 |
| --- | --- | --- | --- | --- | --- |
| Catalyst Composition (wt. ratio) | NiO—$Fe_2O_3$ (50:50) | NiO—$Fe_2O_3$ (50:50) | NiO—$Fe_2O_3$ (50:50) | NiO—$Fe_2O_3$ (50:50) | NiO—$Fe_2O_3$ (19:81) |
| Catalyst Amount (g) | 5 | 5 | 5 | 5 | 5 |
| Catalyst Calcining Temperature (°C.) | 700 | 600 | 500 | 400 | 1000 |
| Reaction Temperature (°C.) | 400 | 400 | 400 | 400 | 400 |
| Supply Rate of Benzoic Acid ($10^{-4}$ mol/min) | 1.20 | 1.20 | 1.20 | 1.20 | 1.20 |
| Supply Rate of Water Vapor ($10^{-3}$ mol/min) | 6.00 | 6.00 | 6.00 | 6.00 | 6.00 |
| Supply Rate of Air (cc/min) | 27 | 27 | 27 | 27 | 27 |
| Supply Rate of Nitrogen Gas (cc/min) | 40 | 40 | 40 | 40 | 40 |
| Conversion of Benzoic Acid (%) | 89 | 94 | 32 | 30 | 0.2 |
| Selectivity (%) |  |  |  |  |  |
| Phenol | 72 | 51 | tr | tr | tr |
| Benzene | 22 | 44 | tr | tr | tr |
| CO, $CO_2$ | 6 | 3 | 100 | 100 | tr |
| Yield of Phenol (%) | 89 × 0.72 | 94 × 0.51 | 32 × tr | 30 × tr | 0.2 × tr |

Example 18

200 g of iron nitrate (FE(NO$_3$)$_3$.9H$_2$O) and 144 g of nickel nitrate (Ni(NO$_3$)$_2$.6H$_2$O) were dissolved in 500 ml of pure water, and about 100 g of sodium hydroxide was dissolved in 500 ml of pure water. Both solutions were added dropwise to 2 l of pure water at ordinary temperature so as to maintain pH 7-8. After adding, the mixture was stirred for about 1 hour. The precipitates produced were filtered and washed. Subsequently, 100 ml of aqueous solution containing 1.62 g of calcium nitrate (Ca(NO$_3$)$_2$. 4H$_2$O) was added to the gelatinous material, and stirred for about 1 hour. The gelatinous material was dried in the atmosphere at 120° C. for 24 hours, and then calcined in the atmosphere at 800° C. for 4 hours to obtain a catalyst having a ratio by weight of 51.4:48.1:0.5 as Fe$_2$O$_3$:NiO:CaO.

Example 19

Using 3.26 g of calcium nitrate, a catalyst was prepared in the same method as Example 18. The catalyst obtained had a ratio by weight of 51.2:47.8:1.0 as Fe$_2$O$_3$:NiO:CaO.

Examples 20,21

200 g of iron nitrate and 144 g of nickel nitrate were dissolved in 500 ml of pure water, and about 100 g of sodium hydroxide was dissolved in 500 ml of pure water. Both solutions were added dropwise to 2 l of pure water at ordinary temperature so as to maintain pH 7-8. After adding, the mixture was stirred for about 1 hour. The precipitates produced were filtered and washed. The cake was dried in the atmosphere at 120° C. for 24 hours, and then calcined in the atmosphere at 800° C. for 4 hours. Subsequently, 49.5 g of the calcined matter was put in 200 ml of aqueous solution containing 2.11 g of calcium nitrate, and evaporated to dryness. The dried matter was further dried at 120° C. for 24 hours, and calcined again in the atmosphere at 500° C. for 3 hours to obtain a catalyst having a ratio by weight of 51.2:47.8:1.0 as Fe$_2$O$_3$:NiO:CaO.

Comparative Examples 5-9

The catalysts prepared in Comparatives Examples 1-4 were used, and the conditions for producing phenol were changed.

Production of Phenol

Each catalyst was crushed and sieved to a prescribed mesh, and the amount described in Table 4 or 5 was placed in a quartz tube having an inner diameter of 20 mm. Benzoic acid, water vapor, air and nitrogen gas were supplied at the rate described in Table 4 or 5, and allowed to react at the temperature described in Table 4 or 5.

The experimental results are summarized in Table 4 and 5.

for 4 hours to obtain a catalyst having a ratio by weight of 51.4:48.1:0.5 as $Fe_2O_3$:NiO:$K_2O$.

Examples 23-26

TABLE 4

|  | Example 18 | Example 19 | Example 20 | Example 21 |
|---|---|---|---|---|
| Catalyst | | | | |
| Composition | $Fe_2O_3$—NiO—CaO | $Fe_2O_3$—NiO—CaO | $Fe_2O_3$—NiO—CaO | $Fe_2O_3$—NiO—CaO |
| (wt. ratio) | (51.4:48.1:0.5) | (51.2:47.8:1.0) | (51.2:47.8:1.0) | (51.2:47.8:1.0) |
| Calcining Temperature (°C.) | 800 | 800 | 800 | 800 |
| Used Amount (ml) | 3.85 | 3.85 | 3.85 | 3.85 |
| Reacting Conditions | | | | |
| Reaction Temperature (°C.) | 400 | 400 | 400 | 400 |
| Supply Gas Concentration (%) | | | | |
| Benzoic Acid | 7.4 | 6.7 | 7.9 | 10.1 |
| Water Vapor | 66.7 | 67.1 | 70.9 | 70.7 |
| Oxygen Gas | 5.2 | 5.2 | 4.3 | 3.8 |
| Nitrogen Gas | 20.7 | 20.9 | 17.0 | 15.4 |
| Space Velocity ($hr^{-1}$) | 7730 | 7760 | 9180 | 10190 |
| Reaction Results | | | | |
| Conversion of Benzoic Acid (%) | 44.2 | 40.0 | 15.4 | 14.6 |
| Selectivty (%) | | | | |
| Phenol | 92.4 | 94.6 | 98.7 | 95.4 |
| Benzene | 7.3 | 4.1 | 1.1 | 3.7 |
| CO, $CO_2$ | 0.3 | 0.3 | tr | tr |
| Yield of Phenol (%) | 44.2 × 0.924 | 40.0 × 0.0946 | 15.4 × 0.987 | 14.6 × 0.954 |
| Space Time Yield of Phenol (g/l.h) | 980 | 826 | 461 | 601 |

TABLE 5

|  | Comparative 5 | Comparative 6 | Comparative 7 | Comparative 8 | Comparative 9 |
|---|---|---|---|---|---|
| Catalyst | | | | | |
| Composition | NiO | $Fe_2O_3$ | $MoO_3$—$V_2O_5$—$CuO$—$Na_2O$—$Al_2O_3$ | $MoO_2$—$V_2O_5$—$CuO$—$Na_2O$—$Al_2O_3$ | CuO—ZnO—$K_2O$—$Al_2O_3$ |
| (wt. ratio) | (100) | (100) | (3.9:3.7:3.8:5.9:82.7) | (3.9:3.7:3.8:5.9:82.7) | (4.0:3.0:3.6:89.4) |
| Calcining Temperature (°C.) | 800 | 800 | 600 | 800 | 500 |
| Used Amount (ml) | 1.9 | 1.9 | 5.9 | 3.85 | 5.3 |
| Reacting Conditions | | | | | |
| Reaction Temperature (°C.) | 400 | 400 | 300 | 300 | 300 |
| Supply Gas Concentration (%) | | | | | |
| Benzoic Acid | 2.3 | 2.3 | 2.3 | 4.0 | 2.3 |
| Water Vapor | 69.9 | 69.9 | 69.9 | 71.0 | 69.9 |
| Oxygen Gas | 4.7 | 4.7 | 4.7 | 5.1 | 4.7 |
| Nitrogen Gas | 23.1 | 23.1 | 23.1 | 20.0 | 23.1 |
| Space Velocity ($hr^{-1}$) | 8200 | 8200 | 2640 | 9380 | 2960 |
| Reaction Results | | | | | |
| Conversion of Benzoic Acid (%) | 8.0 | 0.1 | 47.8 | 16.3 | 25.1 |
| Selectivity (%) | | | | | |
| Phenol | 15.1 | 10.4 | 79.7 | 41.3 | 70.4 |
| Benzene | 15.9 | 3.1 | 2.9 | 14.2 | 4.6 |
| CO, $CO_2$ | 69.0 | 85.3 | 16.3 | 30.5 | 18.7 |
| Yield of Phenol (%) | 8.0 × 0.151 | 0.1 × 0.104 | 47.8 × 0.797 | 16.3 × 0.413 | 25.1 × 0.704 |
| Space Time Yield of Phenol (g/l.h) | 10 | 0.1 | 99 | 96 | 50 |

Example 22

200 g of iron nitrate ($FE(NO_3)_3 \cdot 9H_2O$) and 144 g of nickel nitrate ($Ni(NO_3)_2 \cdot 6H_2O$) were dissolved in 500 ml of pure water, and about 100 g of sodium hydroxide was dissolved in 500 ml of pure water. Both solutions were added dropwise to 2 l of pure water at ordinary temperature so as to maintain pH 7-8. After adding, the mixture was stirred for about 1 hour. The precipitates produced were filtered and washed. The cake was dried in the atmosphere at 120° C. for 24 hours, and then calcined in the atmosphere at 800° C. for 4 hours. Subsequently, 49.75 g of the calcined matter was put in 200 ml of aqueous solution containing 0.30 g of potassium hydroxide (KOH), and evaporated to dryness. The dried matter was dried in the atmosphere at 120° C. for 24 hours, and calcined again in the atmosphere at 800° C.

Using 49.5 g of the calcined matter and 0.6 g of potassium hydroxide, a catalyst was prepared in the same method as Example 22. The catalyst obtained had a ratio by weight of 51.2:47.8:1.0 as $Fe_2O_3$:NiO:$K_2O$.

Example 27

200 g of iron nitrate ($FE(NO_3)_3 \cdot 9H_2O$) and 144 g of nickel nitrate ($Ni(NO_3)_2 \cdot 6H_2O$) were dissolved in 500 ml of pure water, and about 100 g of sodium hydroxide was dissolved in 500 ml of pure water. Both solutions were added dropwise to 2 l of pure water at ordinary temperature so as to maintain pH 7-8. After adding the mixture was stirred for about 1 hour. The precipitates produced were filtered and washed. Subsequently, 100 ml of aqueous solution containing 1.77 g of sodium carbonate ($Na_2CO_3 \cdot 10H_2O$) was added to the gelatinous material and stirred for about 1 hour. The gelatious material was dried in the atmosphere at 120° C. for 24 hours, and then calcined in the atmosphere at 800° C. for 4 hours to obtain a catalyst having a ratio by weight of 51.4:48.1:0.5 as $Fe_2O_3:NiO:Na_2O$.

Examples 28-31

Except of changing the amount of sodium carbonate, various catalysts were prepared in the same method as Example 27. The compositions of the obtained catalysts were 51.7:48.2:0.05, 51.2:47.8:1.0, 50.6:47.4 2.0 and 49.1:45.9:5.0 as the ratio by weight of $Fe_2O_3:NiO:Na_2O$, respectively.

Examples 32-34

Except of changing the calcining temperature, various catalysts were prepared in the same method as Example 27.

Examples 35-38

Except of changing the amount of ferric nitrate and nickel nitrate, various catalysts were prepared in the same method as Example 27. The compositions of the obtained catalysts were 21.0:78.5:0.5, 34.6 64.9:0.5, 62.8:36.7:0.5 and 67.8:31.7:0.5 as the ratio by weight of $Fe_2O_3:NiO:Na_2O$, respectively.

Examples 39-43

200 g of iron nitrate ($FE(NO_3)_3.9H_2O$) and 144 g of nickel nitrate ($Ni(NO_3)_2.6H_2O$) were, dissolved in 500 ml of pure water, and about 100 g of sodium hydroxide was dissolved in 500 ml of pure water. Both solutions were added dropwise to 2 l of pure water at ordinary temperature so as to maintain pH 7-8. After adding the mixture was stirred for about 1 hour. The precipitates produced were filtered and washed. Subsequently, 100 ml of aqueous solution containing 1.77 g of sodium carbonate ($Na_2CO_3.10H_2O$) was added to the gelatinous material, and stirred for about 1 hour. The gelatinous material was dried in the atmosphere at 120° C. for 24 hours, and then calcined in the atmosphere at 800° C. for 4 hours to obtain a catalyst having a ratio by weight of 51.4:48.1:0.5 as $Fe_2O_3:N_2O:Na_2O$.

Example 44

Using 3.75 g of sodium carbonate, a catalyst was prepared in the same method as Examples 39-43. The catalyst obtained had a ratio by weight of 51.2:47.8:1.0 as $Fe_2O_3:NiO:Na_2O$.

Example 45

200 g of iron nitrate ($FE(N_3)_3.9H_2O$) and 144 g of nickel nitrate ($Ni(NO_3)_2.6H_2O$) were dissolved in 500 ml of pure water, and about 100 g of sodium hydroxide was dissolved in 500 ml of pure water. Both solutions were added dropwise to 2 l of pure water at ordinary temperature so as to maintain pH 7-8. After adding, the mixture was stirred for about 1 hour. The precipitates produced were filtered and washed. The cake was dried in the atmosphere at 120° C. for 24 hours, and then calcined in the atmosphere at 800° C. for 4 hours. Subsequently, 49.5 g of the calcined matter was impregnated in 200 ml of aqueous solution containing 0.65 g of sodium hydroxide (NaOH), and evaporated to dryness. The dried matter was dried in the atmosphere at 120° C. for 24 hours, and calcined again in the atmosphere at 500° C. for 3 hours to obtain a catalyst having a ratio by weight of 51.2:47.8:1.0 as $Fe_2O_3:NiO:Na_2O$.

Example 46

Using 2.22 g of sodium carbonate, a catalyst was prepared in the same method as Examples 39-43. The catalyst obtained had a ratio by weight of 51.2:47.8:1.0 as $Fe_2O_3:NiO:Na_2O$.

Comparative Examples 10, 11

Changing the calcining temperature to 500° C. or 1,000° C., catalysts were prepared in the same method as Example 27.

Production of Phenol

Each catalyst was crushed and sieved to a prescribed mesh, and the amount described in Table 6 or 7 was placed in a quartz tube having an inner diameter of 20 mm. Benzoic acid, water vapor, air and nitrogen gas were supplied at the rate described in Table 6 or 7, and allowed to react at the temperature described in Table 6 or 7.

The experimental results are summarized in Table 6 and 7. The experimental results of Comparative Examples 5 to 9 are also shown in Table 7.

TABLE 6-1

|  | Example 22 | Example 23 | Example 24 | Example 25 | Example 26 |
|---|---|---|---|---|---|
| Catalyst |  |  |  |  |  |
| Composition (wt. ratio) | $Fe_2O_3$—NiO—$K_2O$ (51.4:48.1:0.5) | $Fe_2O_3$—NiO—$K_2O$ (51.2:47.8:1.0) | $Fe_2O_3$—NiO—$K_2O$ (51.2:47.8:1.0) | $Fe_2O_3$—NiO—$K_2O$ (51.2:47.8:1.0) | $Fe_2O_3$—NiO—$K_2O$ (51.2:47.8:1.0) |
| Calcining Temperature (°C.) | 800 | 800 | 800 | 800 | 800 |
| Used Amount (ml) | 3.85 | 3.85 | 3.85 | 3.85 | 3.85 |
| Reacting Conditions |  |  |  |  |  |
| Reaction Temperature (°C.) | 400 | 400 | 400 | 400 | 400 |
| Supply Gas Concentration (%) |  |  |  |  |  |
| Benzoic Acid | 6.7 | 7.5 | 3.9 | 7.0 | 3.4 |
| Water Vapor | 66.7 | 75.2 | 70.6 | 63.4 | 83.9 |
| Oxygen Gas | 5.3 | 3.5 | 5.1 | 5.9 | 2.6 |
| Nitrogen Gas | 21.3 | 13.8 | 20.4 | 23.7 | 10.2 |
| Space Velocity ($hr^{-1}$) | 7590 | 11360 | 9180 | 5710 | 3420 |
| Reaction Results |  |  |  |  |  |
| Conversion of Benzoic Acid (%) | 67.9 | 45.6 | 40.4 | 37.2 | 37.0 |
| Selectivity (%) |  |  |  |  |  |
| Phenol | 91.1 | 83.4 | 90.1 | 93.5 | 95.3 |
| Benzene | 8.6 | 13.3 | 5.4 | 6.1 | 3.3 |
| CO, $CO_2$ | 0.3 | 0.6 | 1.3 | 0.2 | 1.3 |

TABLE 6-1-continued

|  | Example 22 | Example 23 | Example 24 | Example 25 | Example 26 |
|---|---|---|---|---|---|
| Yield of Phenol (%) | 67.9 × 0.911 | 45.6 × 0.834 | 40.4 × 0.901 | 37.2 × 0.935 | 37.0 × 0.953 |
| Space Time Yield of Phenol (g/l.h) | 1320 | 1370 | 547 | 588 | 169 |

TABLE 6-2

|  | Example 27 | Example 28 | Example 29 | Example 30 | Example 31 |
|---|---|---|---|---|---|
| Catalyst | | | | | |
| Composition (wt. ratio) | $Fe_2O_3$—NiO—$Na_2O$ (51.4:48.1:0.5) | $Fe_2O_3$—NiO—$Na_2O$ (51.7:48.2:0.05) | $Fe_2O_3$—NiO—$Na_2O$ (51.2:47.8:1.0) | $Fe_2O_3$—NiO—$Na_2O$ (50.6:47.4:2.0) | $Fe_2O_3$—NiO—$Na_2O$ (49.1:45.9:5.0) |
| Calcining Temperature (°C.) | 800 | 800 | 800 | 800 | 800 |
| Used Amount (ml) | 3.85 | 3.85 | 3.85 | 3.85 | 3.85 |
| Reacting Conditions | | | | | |
| Reaction Temperature (°C.) | 400 | 400 | 400 | 400 | 400 |
| Supply Gas Concentration (%) | | | | | |
| Benzoic Acid | 6.8 | 4.8 | 6.7 | 6.7 | 6.7 |
| Water Vapor | 67.6 | 81.0 | 67.1 | 67.1 | 67.1 |
| Oxygen Gas | 5.1 | 2.9 | 5.2 | 5.2 | 5.2 |
| Nitrogen Gas | 20.5 | 11.4 | 20.9 | 20.9 | 20.9 |
| Space Velocity ($hr^{-1}$) | 7700 | 9660 | 7580 | 7610 | 7600 |
| Reaction Results | | | | | |
| Conversion of Benzoic Acid (%) | 95.2 | 31.7 | 72.0 | 71.6 | 73.4 |
| Selectivity (%) | | | | | |
| Phenol | 90.1 | 83.3 | 86.0 | 87.1 | 49.2 |
| Benzene | 7.6 | 15.2 | 11.5 | 12.9 | 46.3 |
| CO, $CO_2$ | 1.9 | 1.5 | 0.7 | 0.1 | 1.3 |
| Yield of Phenol (%) | 95.2 × 0.901 | 31.7 × 0.833 | 72.0 × 0.860 | 71.6 × 0.871 | 73.4 × 0.492 |
| Space Time Yield of Phenol (g/l.h) | 1885 | 514 | 1320 | 1334 | 772 |

TABLE 6-3

|  | Example 32 | Example 33 | Example 34 | Example 35 | Example 36 |
|---|---|---|---|---|---|
| Catalyst | | | | | |
| Composition (wt. ratio) | $Fe_2O_3$—NiO—$Na_2O$ (51.4:48.1:0.5) | $Fe_2O_3$—NiO—$Na_2O$ (51.4:48.1:0.5) | $Fe_2O_3$—NiO—$Na_2O$ (51.4:48.1:0.5) | $Fe_2O_3$—NiO—$Na_2O$ (21.0:78.5:0.5) | $Fe_2O_3$—NiO—$Na_2O$ (34.6:64.9:0.5) |
| Calcining Temperature (°C.) | 700 | 600 | 900 | 800 | 800 |
| Used Amount (ml) | 3.85 | 3.85 | 3.85 | 3.85 | 3.85 |
| Reacting Conditions | | | | | |
| Reaction Temperature (°C.) | 400 | 400 | 400 | 400 | 400 |
| Supply Gas Concentration (%) | | | | | |
| Benzoic Acid | 6.8 | 6.7 | 6.4 | 6.7 | 6.7 |
| Water Vapor | 67.6 | 67.1 | 67.7 | 67.2 | 67.1 |
| Oxygen Gas | 5.1 | 5.2 | 5.2 | 5.2 | 5.2 |
| Nitrogen Gas | 20.5 | 20.9 | 20.7 | 20.9 | 20.9 |
| Space Velocity ($hr^{-1}$) | 7920 | 7760 | 7340 | 7930 | 7330 |
| Reaction Results | | | | | |
| Conversion of Benzoic Acid (%) | 91.3 | 83.7 | 50.3 | 79.5 | 91.2 |
| Selectivity (%) | | | | | |
| Phenol | 79.6 | 75.1 | 60.7 | 76.3 | 90.5 |
| Benzene | 17.9 | 21.6 | 23.5 | 14.9 | 7.3 |
| CO, $CO_2$ | 2.5 | 3.3 | 15.8 | 8.8 | 2.2 |
| Yield of Phenol (%) | 91.3 × 0.796 | 83.7 × 0.751 | 50.3 × 0.607 | 79.5 × 0.763 | 91.2 × 0.905 |
| Space Time Yield of Phenol (g/l.h) | 1642 | 1370 | 602 | 1352 | 1701 |

TABLE 6-4

|  | Example 37 | Example 38 | Example 39 | Example 40 | Example 41 |
|---|---|---|---|---|---|
| Catalyst | | | | | |
| Composition (wt. ratio) | $Fe_2O_3$—NiO—$Na_2O$ (62.8:36.7:0.5) | $Fe_2O_3$—NiO—$Na_2O$ (67.8:31.7:0.5) | $Fe_2O_3$—NiO—$Na_2O$ (51.4:48.1:0.5) | $Fe_2O_3$—NiO—$Na_2O$ (51.4:48.1:0.5) | $Fe_2O_3$—NiO—$Na_2O$ (51.4:48.1:0.5) |
| Calcining Temperature (°C.) | 800 | 800 | 800 | 800 | 800 |
| Used Amount (ml) | 3.85 | 3.85 | 3.85 | 3.85 | 3.85 |

TABLE 6-4-continued

|  | Example 37 | Example 38 | Example 39 | Example 40 | Example 41 |
|---|---|---|---|---|---|
| Reacting Conditions |  |  |  |  |  |
| Reaction Temperature (°C.) | 400 | 400 | 350 | 370 | 400 |
| Supply Gas Concentration (%) |  |  |  |  |  |
| Benzoic Acid | 6.8 | 6.6 | 7.6 | 7.7 | 7.8 |
| Water Vapor | 67.1 | 67.3 | 70.4 | 69.2 | 69.8 |
| Oxygen Gas | 5.2 | 5.2 | 4.4 | 4.6 | 4.5 |
| Nitrogen Gas | 20.9 | 20.9 | 17.6 | 18.5 | 18.0 |
| Space Velocity ($hr^{-1}$) | 7780 | 7760 | 8590 | 8440 | 8700 |
| Reaction Results |  |  |  |  |  |
| Conversion of Benzoic Acid (%) | 88.6 | 65.8 | 46.0 | 67.7 | 83.8 |
| Selectivity (%) |  |  |  |  |  |
| Phenol | 68.1 | 43.5 | 87.6 | 84.3 | 89.5 |
| Benzene | 28.6 | 54.4 | 12.5 | 13.1 | 9.0 |
| CO, $CO_2$ | 3.3 | 2.1 | tr | tr | 0.4 |
| Yield of Phenol (%) | 88.6 × 0.681 | 65.8 × 0.435 | 46.0 × 0.876 | 67.7 × 0.843 | 83.8 × 0.895 |
| Space Time Yield of Phenol (g/l.h) | 1339 | 615 | 1104 | 1556 | 2121 |

TABLE 6-5

|  | Example 42 | Example 43 | Example 44 | Example 45 | Example 46 |
|---|---|---|---|---|---|
| Catalyst |  |  |  |  |  |
| Composition | $Fe_2O_3$—NiO—$Na_2O$ | $Fe_2O_3$—NiO—$Na_2O$ | $Fe_2O_3$—NiO—$Na_2O$ | $Fe_2O_3$—NiO—$Na_2O$ | $Fe_2O_3$—NiO—$Na_2O$ |
| (wt. ratio) | (51.4:48.1:0.5) | (51.4:48.1:0.5) | (51.2:47.8:1.0) | (51.2:47.8:1.0) | (51.2:47.8:1.0) |
| Calcining Temperature (°C.) | 800 | 800 | 800 | 800 | 800 |
| Used Amount (ml) | 3.85 | 3.85 | 3.85 | 3.85 | 3.85 |
| Reacting Conditions |  |  |  |  |  |
| Reaction Temperature (°C.) | 425 | 450 | 400 | 400 | 400 |
| Supply Gas Concentration (%) |  |  |  |  |  |
| Benzoic Acid | 7.7 | 7.7 | 5.2 | 4.0 | 5.9 |
| Water Vapor | 69.2 | 69.2 | 72.5 | 71.1 | 70.6 |
| Oxygen Gas | 4.6 | 4.6 | 4.6 | 5.0 | 4.7 |
| Nitrogen Gas | 18.5 | 18.5 | 17.8 | 19.9 | 18.8 |
| Space Velocity ($hr^{-1}$) | 8830 | 8730 | 8770 | 9360 | 8300 |
| Reaction Results |  |  |  |  |  |
| Conversion of Benzoic Acid (%) | 76.9 | 89.4 | 76.9 | 100 | 53.9 |
| Selectivity (%) |  |  |  |  |  |
| Phenol | 81.8 | 69.3 | 87.5 | 91.1 | 81.7 |
| Benzene | 17.1 | 23.6 | 10.7 | 7.8 | 15.0 |
| CO, $CO_2$ | 0.9 | 3.8 | 0.4 | 0.6 | 2.0 |
| Yield of Phenol (%) | 76.9 × 0.818 | 89.4 × 0.693 | 76.9 × 0.875 | 100 × 0.911 | 53.9 × 0.817 |
| Space Time Yield of Phenol (g/l.h) | 1797 | 1675 | 1288 | 1430 | 905 |

TABLE 7

|  | Comparative 5 | Comparative 6 | Comparative 7 | Comparative 8 |
|---|---|---|---|---|
| Catalyst |  |  |  |  |
| Composition | NiO | $Fe_2O_3$ | $MoO_3$—$V_2O_5$—CuO—$Na_2O$—$Al_2O_3$ | $MoO_3$—$V_2O_5$—CuO—$Na_2O$—$Al_2O_3$ |
| (wt. ratio) | (100) | (100) | (3.9:3.7:3.8:5.9:82.7) | (3.9:3.7:3.8:5.9:82.7) |
| Calcining Temperature (°C.) | 800 | 800 | 600 | 600 |
| Used Amount (ml) | 1.9 | 1.9 | 5.9 | 3.85 |
| Reacting Conditions |  |  |  |  |
| Reaction Temperature (°C.) | 400 | 400 | 300 | 300 |
| Supply Gas Concentration (%) |  |  |  |  |
| Benzoic Acid | 2.3 | 2.3 | 2.3 | 4.0 |
| Water Vapor | 69.9 | 69.9 | 69.9 | 71.0 |
| Oxygen Gas | 4.7 | 4.7 | 4.7 | 5.1 |
| Nitrogen Gas | 23.1 | 23.1 | 23.1 | 20.0 |
| Space Velocity ($hr^{-1}$) | 8200 | 8200 | 2640 | 9380 |
| Reaction Results |  |  |  |  |
| Conversion of Benzoic Acid (%) | 8.0 | 0.1 | 47.8 | 16.3 |
| Selectivity (%) |  |  |  |  |
| Phenol | 15.1 | 10.4 | 79.7 | 41.3 |
| Benzene | 15.9 | 3.1 | 2.9 | 14.2 |
| CO, $CO_2$ | 69.0 | 85.3 | 16.3 | 30.5 |

TABLE 7-continued

| | | | | |
|---|---|---|---|---|
| Yield of Phenol (%) | 8.0 × 0.151 | 0.1 × 0.104 | 47.8 × 0.797 | 16.3 × 0.413 |
| Space Time Yield of Phenol (g/l.h) | 10 | 0.1 | 99 | 96 |

| | | Comparative 9 | Comparative 10 | Comparative 11 |
|---|---|---|---|---|
| Catalyst | | | | |
| | Composition | $CuO-ZnO-K_2O-Al_2O_3$ | $Fe_2O_3-NiO-Na_2O$ | $Fe_2O_3-NiO-Na_2O$ |
| | (wt. ratio) | (4.0:3.0:3.6:89.4) | (51.4:48.1:0.5) | (51.4:48.1:0.5) |
| | Calcining Temperature (°C.) | 500 | 500 | 1000 |
| | Used Amount (ml) | 5.3 | 3.85 | 3.85 |
| Reacting Conditions | | | | |
| | Reaction Temperature (°C.) | 300 | 400 | 400 |
| Supply Gas Concentration (%) | | | | |
| | Benzoic Acid | 2.3 | 6.7 | 6.7 |
| | Water Vapor | 69.9 | 67.1 | 67.1 |
| | Oxygen Gas | 4.7 | 5.2 | 5.2 |
| | Nitrogen Gas | 23.1 | 20.9 | 20.9 |
| | Space Velocity ($hr^{-1}$) | 2960 | 7780 | 7630 |
| Reaction Results | | | | |
| | Conversion of Benzoic Acid (%) | 25.1 | 11.8 | 0.1 |
| Selectivity (%) | | | | |
| | Phenol | 70.4 | 1.1 | tr |
| | Benzene | 4.6 | 7.6 | tr |
| | CO, $CO_2$ | 18.7 | 91.3 | tr |
| | Yield of Phenol (%) | 25.1 × 0.704 | 11.8 × 0.11 | tr |
| | Space Time Yield of Phenol (g/l.h) | 50 | 3 | tr |

Example 47-49

200 g of iron nitrate ($FE(NO_3)_3.9H_2O$) and 144 g of nickel nitrate ($Ni(NO_3)_2.6H_2O$) were dissolved in 500 ml of pure water, and about 100 g of sodium hydroxide was dissolved in 500 ml of pure water. Both solutions were added dropwise to 2 l of pure water at ordinary temperature so as to maintain pH 7-8. After adding, the mixture was stirred for about 1 hour. The precipitates produced were filtered and washed. Subsequently, 100 ml of aqueous solution containing 1.77 g of sodium carbonate ($Ni_2CO_3.10H_2O$) and 0.16 g of calcium nitrate ($Ca(NO_3)_2.4H_2O$) were added to the gelatinous material, and stirred for about 1 hour. The gelatinous material was dried in the atmosphere at 120° C. for 24 hours, and then calcined in the atmosphere at 800° C. for 4 hours to obtain a catalyst having a ratio by weight of 51.4:48.1:0.5:0.05 as $Fe_2O_3:NiO:Na_2O:CaO$.

Example 50

Using 1.62 g of calcium nitrate, a catalyst was prepared in the some method as Examples 47-49. The catalyst obtained had a ratio by weight of 51.2:47.8:0.5 0.5 as $Fe_2O_3:NiO:Na_2O:CaO$.

Production of Phenol

Each catalyst was crushed and sieved to a prescribed mesh, and the amount described in Table 8 was placed in a quartz tube having an inner diameter of 20 mm. Benzoic acid, water vapor, air and nitrogen gas were supplied at the rate described in Table 8, and allowed to react at the temperature described in Table 8.

The experimental results are summarized in Table 8.

TABLE 8

| | Example 47 | Example 48 | Example 49 | Example 50 |
|---|---|---|---|---|
| Catalyst | | | | |
| Composition | $Fe_2O_3-NiO-Na_2O-CaO$ | $Fe_2O_3-NiO-Na_2O-CaO$ | $Fe_2O_3-NiO-Na_2O-CaO$ | $Fe_2O_3-NiO-Na_2O-CaO$ |
| (wt. ratio) | (51.4:48.1:0.5:0.05) | (51.4:48.1:0.5:0.05) | (51.4:48.1:0.5:0.05) | (51.2:47.8:0.5:0.5) |
| Calcining Temperature (°C.) | 800 | 800 | 800 | 800 |
| Used Amount (ml) | 3.85 | 3.85 | 3.85 | 3.85 |
| Reacting Conditions | | | | |
| Reaction Temperature (°C.) | 400 | 400 | 400 | 400 |
| Supply Gas Concentration (%) | | | | |
| Benzoic Acid | 6.8 | 7.8 | 7.9 | 7.3 |
| Water Vapor | 67.6 | 69.8 | 71.4 | 65.7 |
| Oxygen Gas | 5.1 | 4.5 | 4.1 | 5.4 |
| Nitrogen Gas | 20.5 | 18.0 | 16.5 | 21.6 |
| Space Velocity ($hr^{-1}$) | 7350 | 8770 | 9970 | 7630 |
| Reaction Results | | | | |
| Conversion of Benzoic Acid (%) | 93.7 | 78.3 | 68.7 | 74.8 |
| Selectivity (%) | | | | |
| Phenol | 93.1 | 92.0 | 91.4 | 87.6 |
| Benzene | 5.9 | 6.8 | 6.5 | 11.5 |
| CO, $CO_2$ | tr | tr | 0.5 | 2.0 |
| Yield of Phenol (%) | 93.7 × 0.931 | 78.3 × 0.920 | 68.7 × 0.914 | 74.8 × 0.876 |
| Space Time Yield of Phenol | 1829 | 2053 | 2086 | 1531 |

TABLE 8-continued

|  | Example 47 | Example 48 | Example 49 | Example 50 |
|---|---|---|---|---|
| (g/l.h) | | | | |

We claim:

1. A process for producing phenol from benzoic acid which comprises contacting benzoic acid and gaseous oxygen, the amount of the gaseous oxygen supplied being 0.5 to 50 times moles of the amount of benzoic acid supplied, in the vapor phase with a catalyst for producing phenol consisting essentially of a nickel compound supported on a metal oxide carrier at 200° to 600° C. in the presence of water vapor in a reaction apparatus, and then removing the phenol produced from the reaction apparatus.

2. The process of claim 1 wherein said nickel compound is nickel oxide and said metal oxide carrier is titania, magnesia or α-alumina.

3. The process of claim 2 which is conducted through vapor phase oxidation.

4. The process of claim 3 wherein said catalyst further contains at least one alkali metal compound or an alkaline earth metal compound.

5. The process of claim 4 wherein both of said alkali metal compound and alkaline earth metal compound are oxides.

6. The process of claim 4 wherein said alkali metal compound is sodium oxide or potassium oxide and said alkaline earth metal compound is calcium oxide.

7. The process of claim 5 wherein said alkali metal compound is sodium oxide or potassium oxide and said alkaline earth metal compound is calcium oxide.

8. The process of claim 4 wherein the content of nickel oxide is 2 to 20 wt% and the content of the sum of the alkali metal oxide and the alkaline earth metal oxide is 0.5 to 5 wt%.

9. The process of claim 5 wherein the content of nickel oxide is 2 to 20 wt% and the content of the sum of the alkali metal oxide and the alkaline earth metal oxide is 0.5 to 5 wt%.

10. A process for producing phenol from benzoic acid which comprises contacting benzoic acid and gaseous oxygen, the amount of the gaseous oxygen supplied being 0.5 to 50 times moles of the amount of benzoic acid supplied, in the vapor phase with a catalyst for producing phenol consisting essentially of iron oxide and nickel oxide at 200° to 600° C. in the presence of water vapor in a reaction apparatus, and then removing the phenol produced from the reaction apparatus.

11. The process of claim 10 which is conducted through vapor phase oxidation.

12. The process of claim 11 wherein the ratio by weight of nickel oxide/iron oxide is 0.1 to 10.

13. The process of claim 11 wherein the ratio by weight of nickel oxide/iron oxide is 0.5 to 2.

14. The process of claim 11 wherein said catalyst further contains an alkali metal compound.

15. The process of claim 14 wherein said alkali metal compound is an oxide, hydroxide, carbonate, or nitrate.

16. The process of claim 14 wherein said alkali metal compound is an oxide.

17. The process of claim 16 wherein said oxide is sodium oxide or potassium oxide.

18. The process of claim 14 wherein the content of the alkali metal compound converted to the oxide thereof is 0.05 to 30 wt%.

19. The process of claim 18 wherein the ratio by weight of nickel oxide/iron oxide is 0.1 to 10.

20. The process of claim 11 wherein said catalyst further contains an alkaline earth metal compound.

21. The process of claim 20 wherein said alkaline earth metal compound is an oxide, hydroxide, carbonate, or nitrate.

22. The process of claim 20 wherein said alkaline earth metal compound is an oxide.

23. The process of claim 22 wherein said oxide is calcium oxide.

24. The process of claim 20 wherein the content of the alkaline earth metal compound converted to the oxide thereof is 0.05 to 30 wt%.

25. The process of claim 24 wherein the ratio by weight of nickel oxide/iron oxide 0.1 to 10.

26. The process of claim 11 wherein said catalyst further contains an alkali metal compound and an alkaline earth metal compound.

27. The process of claim 26 wherein both of said alkali metal compound and alkaline earth metal compound are oxides.

28. The process of claim 26 wherein said alkali metal compound is sodium oxide and said alkaline earth metal compound is calcium oxide.

29. The process of claim 26 wherein the content of the alkali metal compound converted to the oxide thereof is 0.01 to 20 wt% and the content of the alkaline earth metal compound converted to the oxide thereof is 0.01 to 20 wt%.

30. The process of claim 29 wherein the ratio by weight of nickel oxide/iron oxide is 0.1 to 10.

31. The process of claim 10 wherein the catalyst is supported on a metal oxide carrier.

32. The process of claim 10 wherein the catalyst is produced by calcining a mixture of iron oxide or a precursor thereof with a nickel oxide or a precursor thereof at a temperature of 600° to 900° C.

33. A process for producing phenol from benzoic acid which comprises contacting benzoic acid and gaseous oxygen, the amount of the gaseous oxygen supplied being 0.5 to 50 times moles of the amount of benzoic acid supplied, in the vapor phase with a catalyst for producing phenol wherein the active component for oxidizing benzoic acid to produce phenol consists essentially of a nickel compound supported on a metal oxide carrier at 200° to 600° C. in the presence of water vapor in a reaction apparatus, and then removing the phenol produced from the reaction apparatus.

34. A process for producing phenol from benzoic acid which comprises contacting benzoic acid and gaseous oxygen, the amount of the gaseous oxygen supplied being 0.5 to 50 times moles of the amount of benzoic acid supplied, in the vapor phase with a catalyst for producing phenol consisting essentially of a nickel compound supported on a metal oxide carrier At 200° to 600° C. in the presence of water vapor in a reaction apparatus, and then removing the phenol produced from the reaction apparatus, wherein said catalyst has a conversion of benzoic acid of more than 49% and a selectivity to phenol of more than 57%.

35. A process for producing phenol from benzoic acid which comprises contacting benzoic acid and gaseous oxygen, the amount of the gaseous oxygen supplied being 0.5 to 50 times moles of the amount of benzoic acid supplied, in the vapor phase with a catalyst for producing phenol consisting of a nickel compound supported on a metal oxide carrier At 200° to 600° C. in the presence of water vapor in a reaction apparatus, and then removing the phenol produced from the reaction apparatus.

36. The process of claim 34, wherein the conversion of benzoic acid is more than 87% and the selectivity to phenol is more than 64%.

37. A process for producing phenol from benzoic acid which comprises contacting benzoic acid and gaseous oxygen, the amount of the gaseous oxygen supplied being 0.5 to 50 times moles of the amount of benzoic acid supplied, in the vapor phase with a catalyst for producing phenol wherein the active component for oxidizing benzoic acid to produce phenol consists essentially of iron oxide and nickel oxide at 200° to 600° C. in the presence of water vapor in a reaction apparatus, and then removing the phenol produced from the reaction apparatus.

38. A process for producing phenol from benzoic acid which comprises contacting benzoic acid and gaseous oxygen, the amount of the gaseous oxygen supplied being 0.5 to 50 times moles of the amount of benzoic acid supplied, in the vapor phase with a catalyst for producing phenol consisting essentially of iron oxide and nickel oxide at 200° to 600° C. in the presence of water vapor in a reaction apparatus, and then removing the phenol produced from the reaction apparatus, wherein said catalyst has a conversion of benzoic acid of more than 40% and a selectivity to phenol of more than 49.2%.

39. A process for producing phenol from benzoic acid which comprises contacting benzoic acid and gaseous oxygen, the amount of the gaseous oxygen supplied being 0.5 to 50 times moles of the amount of benzoic acid supplied, in the vapor phase with a catalyst for producing phenol consisting of iron oxide and nickel oxide at 200° to 600° C. in the presence of water vapor in a reaction apparatus, and then removing the phenol produced from the reaction apparatus.

40. The process of claim 38, wherein the conversion of benzoic acid is more than 67.7% and the selectivity to phenol is more than 69.3%.

* * * * *